United States Patent [19]

Stark et al.

[11] Patent Number: 5,542,575
[45] Date of Patent: Aug. 6, 1996

[54] LIQUID REAGENT CONTAINER HAVING A PRIMARY AND SECONDARY CLOSURE MECHANISM

[75] Inventors: William A. Stark; Ernest H. Pfadenhauer, both of Costa Mesa, Calif.

[73] Assignee: Dade Interantional Inc., Deerfield, Ill.

[21] Appl. No.: 89,132

[22] Filed: Jul. 9, 1993

[51] Int. Cl.$^6$ .................................................. B65D 47/26
[52] U.S. Cl. ........................ 220/256; 220/348; 220/545
[58] Field of Search .................................. 220/256, 262, 220/345, 346, 348, 379; 215/322; 222/545, 559, 561

[56] References Cited

U.S. PATENT DOCUMENTS

| | | |
|---|---|---|
| 842,444 | 1/1907 | Brundrett . |
| 882,547 | 3/1908 | Chellis et al. . |
| 1,102,275 | 7/1914 | Kime .................... 220/348 X |
| 1,170,233 | 2/1916 | Foster . |
| 1,227,463 | 5/1917 | Luyties ...................... 220/256 |
| 1,320,067 | 10/1919 | Kowalski ................ 220/348 X |
| 1,399,759 | 12/1921 | Fulenwider . |
| 1,473,162 | 11/1923 | Sage . |
| 1,572,505 | 2/1926 | Raymond . |
| 1,614,236 | 1/1927 | Druiff . |
| 1,802,359 | 4/1931 | Tone . |
| 1,857,465 | 5/1932 | Maker et al. . |
| 1,944,551 | 1/1934 | Forknall . |
| 2,041,259 | 5/1936 | Morrison ................... 220/256 |
| 2,582,360 | 1/1952 | Sheridan . |
| 2,604,231 | 7/1952 | Probstein . |
| 2,657,829 | 11/1953 | Walch .................... 220/348 X |
| 2,950,833 | 8/1960 | Short . |
| 2,961,119 | 11/1960 | Leach . |
| 3,352,445 | 11/1967 | Cochin . |
| 3,904,062 | 9/1975 | Grussen . |
| 3,938,690 | 2/1976 | Butler . |
| 4,059,167 | 11/1977 | Lee . |
| 4,455,280 | 6/1984 | Shinohara et al. . |
| 4,520,940 | 6/1985 | Boyd et al. . |
| 4,805,790 | 2/1989 | Leonetti et al. . |
| 4,896,780 | 1/1990 | Jessop et al. . |
| 4,949,865 | 8/1990 | Turner . |
| 5,005,721 | 4/1991 | Jordan . |
| 5,064,086 | 11/1991 | McEntee . |
| 5,083,672 | 1/1992 | Lewandowski ........................ 215/322 |

FOREIGN PATENT DOCUMENTS

| | | |
|---|---|---|
| 0287005 | 10/1988 | European Pat. Off. . |
| 1120605 | 1/1955 | France . |

*Primary Examiner*—Joseph M. Moy
*Attorney, Agent, or Firm*—Kurt A. MacLean

[57] ABSTRACT

The invention disclosed is a sealed fluent material container having a chamber with an opening provided with a manually operable primary closure mechanism and a secondary closure mechanism that may be operated either manually or automatically. Manual removal of the primary closure mechanism from the chamber opening allows the secondary closure mechanism to extend a laterally moveable tongue from a horizontal guide recess on the top of the container to a normally closed position covering the opening. An engagable tab on the secondary closure permits the retraction of the moveable tongue against the biasing means to expose the chamber opening. The container has particular utility for use in automated chemical dispensers, analyzers and related equipment for the analysis and testing of blood, physiological fluids and other biological samples.

18 Claims, 2 Drawing Sheets

LIQUID REAGENT CONTAINER HAVING A PRIMARY AND SECONDARY CLOSURE MECHANISM

FIELD OF THE INVENTION

The present invention relates to a fluent material container suitable for use with automated chemical dispensers and related equipment. More particularly, the invention relates to a sealed container having a chamber with an opening, a manually operable primary closure mechanism and a secondary closure mechanism that may be operated either manually or automatically. Removal of the primary closure mechanism from the chamber opening allows the secondary closure, in the form of a resiliently biased laterally moveable tongue, to extend from a guide recess to a normally closed position covering the opening. An engagable tab on the secondary closure mechanism permits the retraction of the moveable tongue against the biasing mechanism to expose the chamber opening. The present invention has particular utility for use in automated chemical analyzers and related equipment for the analysis and testing of blood, physiological fluids and other biological samples.

BACKGROUND OF THE INVENTION

A wide variety of automated clinical analyzers are known in the art and widely used in hospitals, clinics, and research laboratories. A particularly popular example of such a device is the multi-channel type analyzer in which a series of different tests are performed simultaneously and in parallel with one another. The typical multi-channel analyzer generally utilizes liquid or solid reagents to react with a particular constituent present in a sample. Reaction parameters are then monitored using a photometric system or electrically sensitive probes to determine reaction rates, sample constituent concentrations or other similar characteristics.

The usual method employed for performing photometric procedures is to place the sample solution in a small cell, tube, or cuvette provided with transparent walls and interposing the sample solution between a light source and a photosensitive detecting element. When electrical parameters such as ion concentration are to be determined, a probe is actually immersed in the mixture of reagent and sample. In order to perform multiple tests on each sample, most contemporary multi-channel analyzers incorporate several liquid reagent storage reservoirs along with automated transfer and dispensing devices such as aspirating probes. Small aliquots of the sample are combined with the appropriate reagents and evaluated using appropriate techniques.

Although multi-channel automated analyzers incorporating liquid reagent technology have received wide acceptance, there are certain drawbacks associated with their use. For example, to repeatedly provide precise and accurate results, the liquid reagents employed in sample processing must be of consistent quality and uniform concentration. Simple mistakes or reagent degradation can render entire sample runs useless with adverse economic consequences and potentially serious results. As a result relatively labor intensive protocols must be implemented to ensure reagent consistency. Further, to maintain the necessary level of homogeneity between sample runs or reagent lots, highly trained personnel are required to operate clinical analyzers driving up the per unit test cost.

Such concerns are exacerbated by the inherent lack of stability found in a number of the reagents most useful for the analysis of biological samples. Many commonly used liquid reagents are susceptible to external environmental factors which can cause degradation of the active compound. For example, the properties of certain reagents may be altered by excessive exposure to atmospheric components such as oxygen or water. Reagents may also be degraded through exposure to light or elevated temperatures. Such degradation may lead to a reduction in reagent activity or the production of contaminating artifacts which can adversely affect sample runs.

In addition to degradation, many reagents employed in the automatic analysis of biological samples contain volatile components. In the analyzer these reagents are usually kept in temperature controlled compartments to ensure uniform sample runs. When these reagents are used in an atmospheric environment for extended periods, substantial changes in reagent concentration may occur and distort test results. Further, reagents which experience evaporation of some constituent may undergo an increase in viscosity so that they do not dispense accurately. In extreme cases, the reagent may evaporate to the point of leaving a crust of solids which blocks the dispensing mechanism used for that reagent.

Conversely, in humid or refrigerated environments the possibility of absorption or condensation of gaseous water from the operating environment may actually decrease the effective concentration of particular reagents over time. Similar additive discrepancies in reagent concentration can occur where contaminants fall or drip into the open reagent container over time.

While liquid reagent containers may be fitted with modified caps which allow the transfer of material while preventing contamination or evaporation, such caps generally interfere with reagent changing procedures and greatly increase the possibility of contamination from external sources if the closures are improperly used or switched between containers. Further, most protective caps and closures must be manually applied and correctly seated each time to operate properly. In the high volume testing environment associated with most chemical analyzers numerous reagent changes or transfers are often required within a short period of time. This greatly increases the likelihood of contamination or evaporation due to the improper use of caps or similar manual safeguards.

Like evaporation or reagent degradation, external contamination can alter the characteristics of the reagent and adversely affect sample runs. While many of the chemical analyzers currently in use have safeguards against reagent contamination built in, these protective measures may be subverted by operator error. For instance, a self cleaning probe is highly ineffective if the liquid reagent has been previously contaminated through the improper use of a screw cap from another container. Other common sources of contamination involve the transfer of bulk reagents to containers suitable for use with the analyzer and splashing between the containers during sample runs or reagent conversions.

Adding to these difficulties many liquid reagents used with automatic analyzers need to be removed daily from their temperature controlled compartment, recapped, and stored in a laboratory refrigerator due to a lack of stability. This method of storage tends to reduce reagent evaporation though it may increase the chances for reagent contamination through operator error. Further, the constant removal and change in physical environment substantially slows sample throughput and greatly increases the cost per unit test. In addition to increased labor demands, the removal and storage of reagents requires extra calibration which, though necessary, increases the time and expense of a sample run. The associated down time is also inflated by the period required for the cold reagents to re-equilibrate to stable operating temperatures. All of these potential difficulties represent significant operating interruptions and expenses that may be experienced with the operation of a clinical analyzer. More importantly, these limitations in reagent availability increase the probability of lost test results for the samples in process, as well as increasing delays in processing other specimens awaiting analysis.

Different procedures have been advanced to resolve these problems but none has proved to be a comprehensive panacea. Initially, liquid reagents were supplied in bulk form and aliquoted into volumes compatible with the analyzing apparatus. Bulk preparation of liquid reagents generally ensures consistent characteristics and reduced calibration for each assay without labor intensive mixing or cleaning. However, potential contamination problems remain and the evaporation difficulties noted above still require the daily removal of the reagents from the analyzer for controlled storage.

More recently, the liquid reagents have been provided in smaller, more convenient volumes, ready for immediate use with the analyzing equipment. Typically, these ready to use reagents are packaged in disposable vials or containers which may be resealable. Yet even if the vials or containers are resealable, the use of manually operated closures still presents several problems. For instance, the individual closure may be misplaced or inadvertently attached to the wrong container possibly contaminating the reagent within. Further, it is inconvenient to individually open and reclose each container in an automatic testing environment where test setup time and the time between tests can have a significant impact on sample throughput. In addition, the use of smaller, individually packaged reagents may increase lot to lot variation in reagents with corresponding down time for additional calibration.

Though effective at overcoming some of the earlier drawbacks associated with bulk reagents, these prior art reagent containers fail to address the need for an adaptable liquid reagent container that will ensure the stability of its contents and retard vaporization or condensation without increasing the likelihood of contamination. Such a container would enhance the ability to store liquid reagents for long periods of time on or in the chemical analyzer. With such a storage container, the analytical instrument would be continuously capable of immediately performing real time tests on biological samples. Further, such storage capabilities would increase the flexibility of the testing apparatus and substantially reduce labor costs on a per test basis. Moreover, it would be of significant benefit to the medical field and related professions to provide a fluent reagent container which reduces the level of skill necessary to effectively operate an automated processing apparatus.

Accordingly, it is an object of the present invention to provide a fluent material container which enhances the stability of stored reagents thereby maintaining the uniformity of the reagent solution over time.

It is an additional object of the present invention to provide a fluent material container which allows a reagent to be maintained in an automatic analyzer operating environment over extended periods of time without significant changes in activity.

It is yet an additional object of the present invention to provide a fluent material container which facilitates the transfer and storage of a reagent while decreasing the risk of reagent contamination.

It is a further object of the present invention to provide a fluent material container that is readily manipulated by modern automated analysis equipment thereby reducing the chance of operator error.

It is an additional object of the present invention to provide a fluent material container that is robust, simple and inexpensive to manufacture and operate, and which provides enhanced operator safety by reducing chemical exposure.

SUMMARY OF THE INVENTION

These and other objects are achieved by the fluent material container of the present invention which, in accordance with broad structural aspects thereof, provides a sealed or normally closed container that will retard the degradation and contamination of reagents under a variety of different conditions yet readily adapts to automated dispensing apparatus while retaining a normally closed configuration when not in use. While the term fluent materials primarily applies to free flowing liquids, other materials such as particulates, flowing solids, gels, and liquids of varying viscosities are also envisioned as being within the scope of this invention. Similarly any fluent material which is subject to degradation or changes in activity over time falls within the scope of this invention.

In addition to the primary manually operable closure mechanism, the fluent materials container disclosed possesses a secondary closure mechanism which effectively and automatically covers the opening of the chamber between sampling thereby safeguarding the integrity of the material within. Moreover, the container of the present invention is uncomplicated and easy to operate making it simple and convenient to use even by relatively unskilled personnel. In addition to being robust and lightweight, the container may be constructed of inexpensive materials such as glass or plastics. Further, the present invention can be quickly and easily removed from an automated analyzer environment to provide a storage vessel adaptable to various conditions.

More specifically, an exemplary embodiment of the reagent container of the present invention includes a liquid tight chamber or receptacle defined by a plurality of side walls, a top surface and a base. The top surface is provided with a generally horizontal opening. The container is provided with both a manually operable primary closure mechanism and a secondary closure mechanism for manually or automatically sealingly closing the opening between sampling or dispensing. Subsequently to removing the primary closure, the secondary closure mechanism may be operated either manually or automatically through an electronically or mechanically controlled assembly designed into a clinical analyzer dispensing mechanism.

In one embodiment of the invention, the primary closure mechanism is formed of an internally threaded cap designed to screw onto a corresponding externally threaded container neck forming the chamber opening which is substantially parallel to the top surface of the chamber. In this embodiment, the removal of the primary closure mechanism from the neck allows the secondary closure mechanism to automatically extend from a guiding recess defined by a housing provided on the top surface of the chamber adjacent to the neck and to sealingly engage and cover the container neck opening. This secondary closure mechanism comprises a spring biased laterally moveable tongue that extends horizontally over the chamber opening in a normally closed position. With the primary closure in place, the laterally moveable tongue partially resides in the guiding recess provided by the housing on the top surface of the chamber. The housing is formed by a raised boss having a substantially horizontal housing cover affixed thereto. While the guiding recess may be horizontal with respect to the top surface of the chamber, in alternative embodiments the guiding recess and the laterally moving tongue residing therein are slightly angled with respect to the top surface of the chamber. Thus, the projecting peripheral lip of the chamber opening may form an angled or conical section with respect to the guiding recess. In such embodiments the mating face of the resiliently biased laterally moveable tongue is correspondingly tapered to allow positive seating of the displaceable tongue on the projecting peripheral lip or neck rim upon extension of the tongue from the recess. Accordingly, the resiliently biased moveable tongue sealingly engages and sits flush on the chamber opening when in its normally closed fully extended position.

Preferably, this laterally moveable tongue is biased to a fully extended or "closed" position by a spring mechanism provided in the housing at a position adjacent to or directly below the housing cover recess. The biasing mechanism interacts with a engagement tab extending downwardly from the laterally moveable tongue thereby transferring the compressive energy of the spring to the laterally moveable tongue and urging it into its extended, normally closed position. An external operating tab on the projecting end of the laterally moveable tongue allows the secondary closure mechanism to be opened against this biasing force either manually or automatically during the sampling cycle by an electronically or mechanically controlled dispensing assembly in an automated system.

In this embodiment of the present invention the reagent container is wedge shaped and designed to fit into a pie shaped sector defined in a rotating carousel. This exemplary embodiment is designed for use in a carousel having eight wedge shaped cavities, each circumscribing an angle of approximately 45°. Once positioned in the carousel with the primary closure removed, each container and enclosed fluent reagent are readily accessible to the automatic dispenser or analyzer at any time yet the container remains closed and covered between cycles.

To obtain the desired reagent for processing a sample, the carousel and reagent containers are positioned appropriately through electro-mechanical means as known in the art. An electrically or mechanically driven dispenser assembly then contacts and applies pressure to the operating tab positioned on the leading edge of the laterally moveable tongue using an automatic contact mechanism. The contact mechanism may be a cam, arm or the like and is preferably driven by an electric solenoid or small motor which is controlled by the analyzer. The contact mechanism applies sufficient horizontal force to the operating tab to overcome the spring bias and force the laterally moveable tongue to retract into the housing guide recess. A reagent transfer tube or dispensing mechanism is then inserted by the analyzer along the vertical axis of the container body through the opening into the chamber where the fluent reagent is contained. After the desired reagent aliquot has been transferred by the dispensing mechanism, the automatic contact mechanism is withdrawn to the point where it is no longer applying force to the operating tab on the laterally moveable tongue. Upon withdrawal of the contact mechanism the spring bias returns the tongue to its normally closed position engaging the projecting peripheral lip and sealing the chamber opening. Thus, the reagent is exposed to potentially degrading factors only as long as the transfer or dispensing apparatus is inserted.

As noted above, an additional aspect of the present invention is the provision of a manually operable primary closure mechanism. In the exemplary embodiment this means for primary closure is formed of an internally threaded screw cap designed to screw onto a correspondingly threaded container neck provided on the chamber opening. When in position to close the opening of the reagent container, the screw cap preferably contacts the projecting leading edge of the laterally moveable tongue thereby retaining the tongue within the guiding recess and inhibiting the extension of the secondary closure across the chamber opening.

Additionally the projecting edge of the laterally moveable tongue may include a racheting pawl designed to interact with friction ridges provided on the outside surface of the screw cap. When in contact with the cap, the pawl interposes itself between the raised friction ridges of the cap allowing it to rotate in only one direction. This additional feature prevents the inadvertent unscrewing and removal of the screw cap yet allows the cap to be tightened by hand when secure mechanical closure of the container in desired.

When removed from the chamber opening, the screw cap may be retained in association with the container by screwing the cap onto a cap holding threaded lug projecting from the housing of the container. By keeping the primary closure mechanism associated with the liquid reagent container, the chances of accidental cap switching and the resultant contamination of the reagent are greatly reduced. Additionally, the projecting stored caps may be used to lift or manipulate the container.

In the normally closed position, the laterally moveable tongue of the secondary closure mechanism automatically closes and protects the chamber opening effectively preventing evaporation, contamination or degradation of reagents therein as well as limiting or preventing harmful chemical exposure to the clinical apparatus or operators that may occur with normally open reagent containers. In its normally closed position the container of the present invention may be easily removed from the analyzer and stored using only the secondary closure mechanism. It is anticipated that reagents stored in this manner will have shelf lives on the order of 90 to 120 days. Alternatively, the container may be removed and positively closed using the screw cap primary closure mechanism. In this alternative configuration the enclosed reagents may be stored for years without problem as the properly positioned screw cap effectively seals the container.

Further, it should be appreciated that the container of the present invention and its positive closure mechanism allows the manufacture and use of interchangeable bulk reagents without the problems of transfer induced contamination or adverse chemical exposure to machine or operator. Thus, in addition to improving and simplifying reagent manipulation and machine operation, the use of the reagent container of the present invention facilitates both inter and intra container reagent consistency which substantially reduces calibration or equilibration problems.

These and additional objects and advantages of the present invention will appear from a reading of the following detailed description of an exemplary embodiment thereof taken in conjunction with the appended drawing figures.

DETAILED DESCRIPTION OF AN EXEMPLARY EMBODIMENT

The fluent materials container of the present invention is applicable to a wide variety of automated sample dispensing, analysis or processing apparatus and provides for the safe, simple, convenient and adaptable storage of reagents used in concert with these devices. Further, the container allows the manipulation and storage of reagents to a degree previously unobtainable in the prior art. As such, the fluent materials container of the present invention is particularly well suited for use in the automated processing or analysis of physiological or biological samples such as blood. Accordingly, while the beneficial features and advantages of the present invention will be discussed in the context of automated sample analysis it should be emphasized that the present invention is not limited to use with these devices. For instance, the present invention exhibits characteristics which make it highly useful in connection with separation technologies such as HPLC or FPLC. Nonetheless, a discussion of the present invention in the context of a multi-channel analyzer apparatus clearly illustrates the features and advantages of the liquid reagent containers and associated closure mechanisms described herein.

As previously detailed, early prior art automated analysis reagent containers typically required a relatively skilled operator to formulate and introduce reagents to the instrument either individually or in multiple position racks. Such labor intensive reagent protocols could result in misformulations and contamination which could compromise entire sample runs. Further, required calibration and re-equilibration times adversely impacted the analysis capabilities of the instrumentation and substantially drove up unit costs. In addition, contamination, degradation and concentration changes brought about by exposed reagent vaporization or condensation and absorption could aggravate discontinuities in existing protocols and invalidate patient test results.

In contrast, the containers of the present invention effectively eliminate the decomposition or alteration of fluent reagents over an extended period of time, often on the order of 90 days or more relying on only the secondary closure mechanism. Conversely, the primary closure mechanism will allow the reagents to be stored for a period of years. Further, the present invention reduces reagent variability by allowing the manufacture and use of bulk reagents without contamination problems. Thus, with the present invention the number of calibration runs required are reduced and the sample throughput of the automated apparatus is correspondingly increased. The present invention also facilitates the transport and storage of liquid reagents resulting in a substantially increased shelf life. Finally, the simplicity of operation of the present invention reduces the need for highly trained and costly personnel to operate the analysis equipment.

Figure 1:
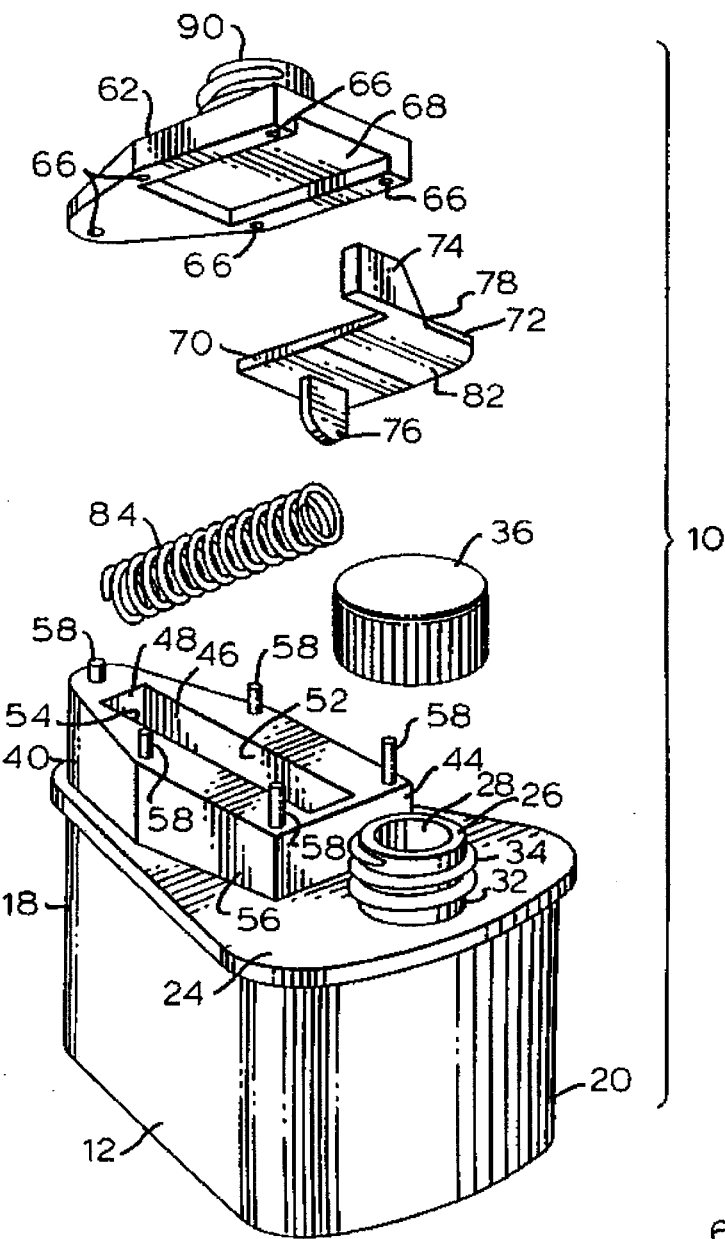
FIG. 1 is an exploded perspective view illustrating an exemplary embodiment of the reagent container of the present invention having both primary and secondary closure mechanisms.
Figure 5:
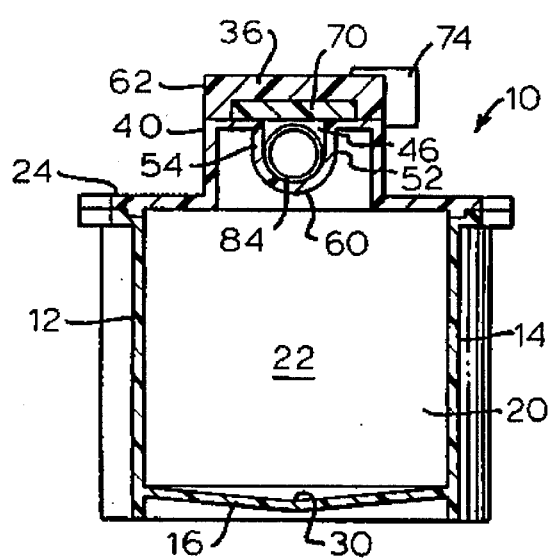
FIG. 5 is a cross-sectional view taken along the plane V—V of FIG. 3 illustrating additional features of the present invention.
Figure 2:
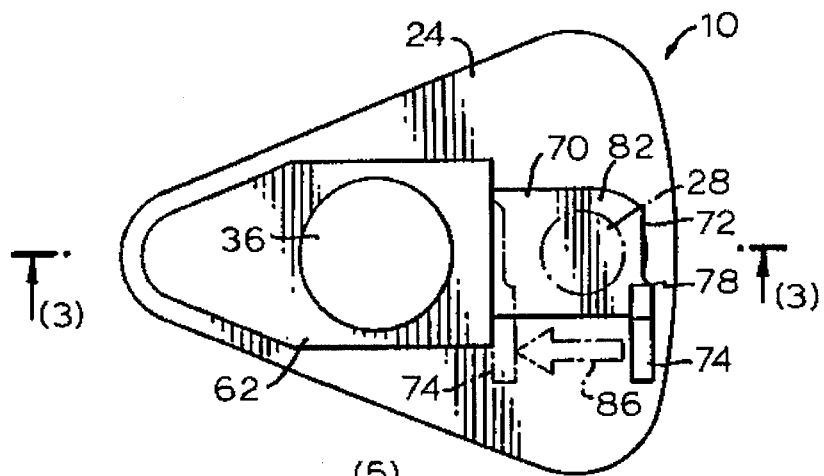
FIG. 2 is a plane view of the embodiment of the invention shown in FIG. 1 illustrating the operation of the secondary closure mechanism.

These features are best illustrated in conjunction with the accompanying figures. Turning first to FIG. 1, an exploded view of the configuration of an exemplary embodiment of a liquid reagent container illustrating the features of the present invention is generally indicated by reference 10. In this exemplary embodiment the container 10 includes side walls 12 and 14 integral with a substantially planar base 16. These side walls 12 and 14, along with a narrow rear end wall 18 and wide front end wall 20 define a fluent containing chamber 22 which is sealed by a correspondingly wedge shaped chamber top 24. Wedge shaped top 24 is provided with a vertically projecting peripheral lip 26 defining an opening 28 to the fluent containing chamber 22. This exemplary embodiment of the present invention includes a fluent material collection point 30 defined by a depending recess in the substantially planar base 16. Fluent materials preferentially accumulate at this point facilitating their removal by an automated dispensing apparatus. The fluent containing chamber 22 and the elements defining it may be more clearly seen in FIG. 5.

While the wedge shaped embodiment of the fluent material container illustrated is demonstrative of the teachings of the present invention, it is in no way essential to its practice. Those skilled in the art will recognize that containers of different configuration may be used within the teachings of the present invention. Similarly, the construction of the chamber is not an essential element and alternative construction techniques are compatible. The illustrated embodiment employs an integrally cast or machined wedge shape chamber having the chamber top 24 sonically welded to the integrally formed wedge to provide a sealed chamber 22 capable of holding fluent materials. However, alternative manufacturing techniques such as blow molding producing equivalent sealed structures are envisioned as being within the scope of this invention and may be utilized based on external factors such as cost or production volume.

The fluent containing chamber and other components of the liquid reagent container of the present invention are preferably formed of inexpensive materials such as plastic, metal or glass. The use of these materials is limited only by their potential reactivity with the enclosed fluent reagent material. Thus, polyvinylchloride, polycarbonate, polypropylene polysulfone, acetate, cellulose and other suitable materials may be utilized to form the container chamber and other components through casting, injection molding, investment molding, machining or other suitable techniques. It should be emphasized that the preferred embodiments of the present invention are particularly suitable for injection molding or casting manufacturing techniques. This greatly simplifies the production process and reduces the associated expense. However, other materials and manufacturing techniques may be used as required by the intended operating environment and reagent compatibility. Thus, temperature or reagent resistant components may be formed from composite materials or glass as needed. Further the materials may be colored or clear depending on the properties of the enclosed reagent. In this context, it should be emphasized that the functions and configurations discussed herein are exemplary only and that alternative configurations may be utilized within the scope and teaching of the present invention.

In the present invention the opening 28 to the fluent containing chamber 22 is defined by a vertically projecting peripheral lip 26 located on the chamber top 24. While the defined opening 28 may be circular to accommodate the designated closures, this shape is not essential and may be modified to enhance its compatibility with the intended operating environment or to ease accessibility. The peripheral lip 26 may define an opening of any size allowing the unimpeded access to the fluent containing chamber 22. Similarly, the position of the opening 28 is not critical and may be established anywhere appropriate on the chamber top 24. In the embodiment of the invention shown in FIGS. 3 and 4 the opening 28 is located near the wide front end wall 20 and directly above the liquid collection point 30. This congruent placement of the opening 28 and liquid collection point 30 maximizes the recovery of fluent reagent during automatic or manual operation of the container.

In the exemplary embodiment of the invention shown in FIG. 1 the vertically projecting peripheral lip 26 is defined by the termination of an integral neck 32 having external threads 34. The lip 26 delineates a substantially circular opening 28 which is distally oriented on the neck 32 with respect to the wedge shaped chamber top 24 and is essentially horizontal. While the embodiment illustrated depicts an elongated integral neck 32, such a configuration is not required to effectively practice the invention. Those skilled in the art will recognize that other embodiments of the invention may position the vertically projecting peripheral lip 26 directly upon the chamber top 24. Selection of a specific embodiment may be based on external factors such as production considerations, the structure of compatible instrumentation and the configuration of other components of the invention.

As illustrated in the embodiment of FIG. 1 neck 32 functions to sealingly engage the primary closure mechanism through manual operation and thereby to sealingly closing chamber opening 28. In this exemplary embodiment the primary closure mechanism is formed as an internally threaded cap 36 that cooperatively engages the external threads 34 of neck 32. Preferably, internally threaded cap 36 engages the external threading 34 on neck 32 and snugly contacts vertically projecting peripheral lip 26. In this embodiment it is preferred that the internally threaded cap 36 be lined with a non-reactive substance such as teflon or the like. Further, to ease the manual manipulation of cap 36 it is preferred that cap 36 be provided with a series of vertically oriented friction ridges 38 along its exterior surface.

While the embodiment illustrated in the figures uses an internally threaded cap as the primary closure mechanism, it should be emphasized that the present invention does not require an externally threaded neck or a cooperatively engaging cap. For example, an alternative embodiment may have a vertically projecting peripheral lip 26 directly adjacent to the chamber top 24 and the primary closure mechanism could be formed of a non-reactive stopper or plug (not shown). Alternative embodiments of this manually operated primary closure mechanism as known in the art are equally compatible with the teachings of the present invention.

As shown in FIG. 1, boss 40 is located on chamber top 24 adjacent to chamber opening 28 defined by vertically projecting peripheral lip 26. Boss 40 is substantially elongated with a distal end 42 contiguous with narrow rear end wall 18 of container 10 and a proximal end 44 adjacent to integral neck 32. An elongated trough 46 is generally centrally positioned along the length of boss 40 and is defined by a distal end wall 46, proximal end wall 48 and side walls 52 and 54. Further, boss 40 is provided with an upper surface 56 having a plurality of locating pins 58 extending vertically therefrom. In the embodiment shown in FIG. 1 the upper surface 56 of the boss is slightly angled with respect to the substantially horizontal chamber top 24.

While boss 40 is shown as elongated and on the exterior side of chamber top 24, its shape and placement are not limited to this arrangement. Those skilled in the art will recognize that alternative configurations of boss 40 may be used to practice the present invention. For instance, upper surface 56 of boss 40 may be angled slightly as shown or may be substantially horizontal, depending on the size and position of the other components of the invention. Other alternative embodiments include the placement of boss 40 on the underside of chamber top 24 within the fluent material containing chamber 22. The position and overall configuration of boss 40 is limited only by the placement of vertically projecting peripheral lip 26 and corresponding opening 28 which should be accessible to the secondary closure mechanism as discussed herein.

Figure 3:
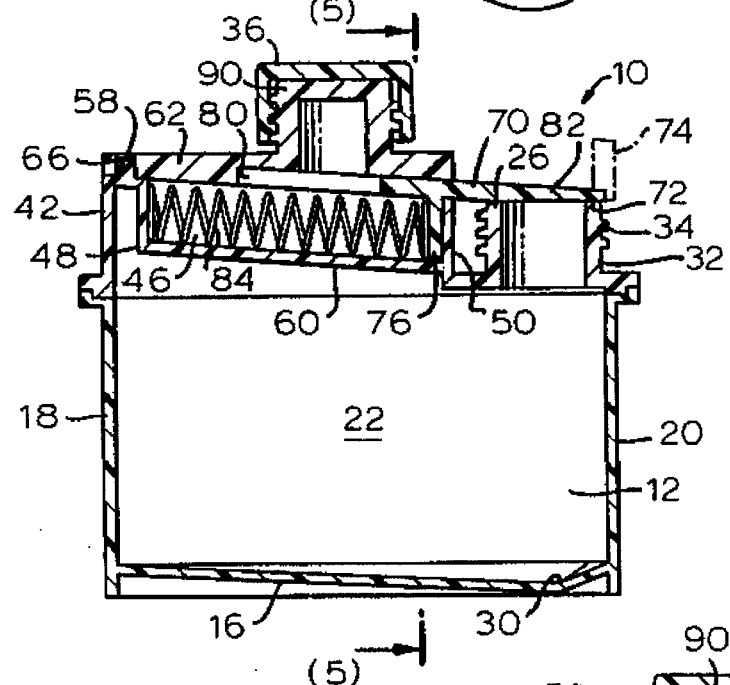
FIG. 3 is a vertical cross-section taken along the plane III—III of FIG. 2.
Figure 4:
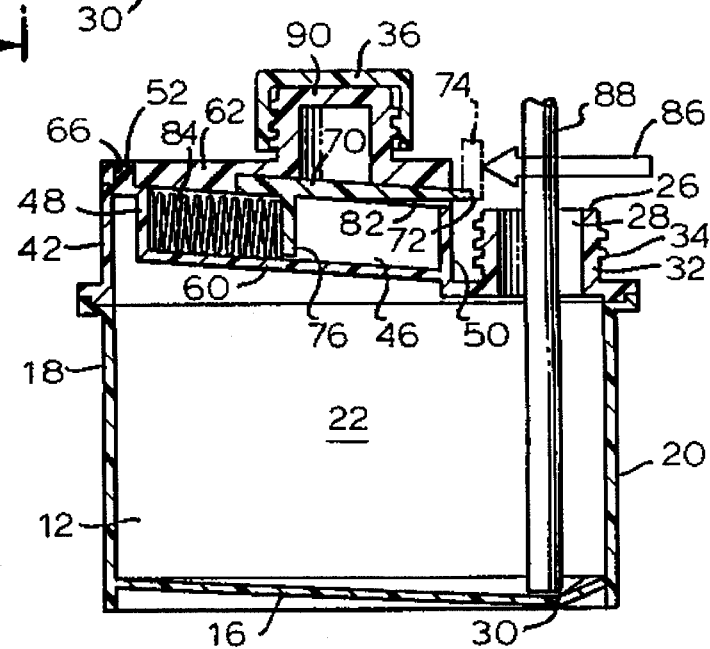
FIG. 4 is a vertical cross-sectional view taken along the plane III—III of FIG. 2 illustrating the secondary closure mechanism in the retracted position.

Similarly, the illustrated shape of trough 46 within boss 40 may have any one of a variety of alternative configurations. In the embodiment shown in FIG. 5 trough 46 is centrally positioned within boss 40 and is provided with an arcuate lower floor 60. FIGS. 3 and 4 show that trough 46 is also angled to a degree corresponding to the angled upper surface of boss 40. Those skilled in the art will appreciate that a variety of equivalent configurations of trough 46 are compatible with the present invention. Alternative embodiments within the scope of the invention may include boss 40 being provided with an off-center trough 46 having a rectangular or angled cross-section, or the like. Further, the length of trough 46 may vary as appropriate.

Container 10 also includes a housing cover 62 affixed to upper surface 56 of boss 40. The lower surface 64 of housing cover 62 is congruous with upper boss surface 56 and defines locating pin cavities 66 designed to receive and accommodate locating pins 58. By affixing housing cover 62 to boss 40, a generally closed housing is formed. Housing cover 62 is provided with an aperture 68 located on its lower surface 64 and, when affixed to boss 40, aperture 68 is proximate to trough 46. The configuration of housing cover 62 is not critical as long as it is congruous with upper boss surface 56 and, when in that position, defines an operative guiding recess 80. Similarly, the method of affixing cover 62 to boss 40 is not critical to the present invention and housing cover 62 may be attached to boss 40 through techniques such as sonic welding, gluing or the like.

As noted, the housing formed by attaching housing cover 62 to boss 40 defines a substantially horizontal guiding recess 80 with aperture 68 comprising its upper surface and vertical walls and the lower surface delineated by upper boss surface 56 and trough 46. The opening of the housing guide recess 80 is proximate to the opening 28 of container 10 as defined by the vertically projecting peripheral lip 26. Positioned within guide recess 80 is a laterally displaceable secondary closure means which in the exemplary embodiment of the present invention comprises tongue 70 having a leading edge 72 projecting from the guide recess 80.

As with boss 40, the position of guiding recess 80 is not critical and it may be placed in various locations as long as it is substantially horizontal with respect to chamber opening 28. In the illustrated embodiment guiding recess 80 is angled slightly downward toward opening 28 thereby directing the secondary closure tongue 70 toward horizontal chamber top 24 upon extension. In the depicted embodiment the slight downward angle of the laterally displaceable tongue 70 provides a natural downward bias to the secondary closure mechanism which increases the pressure of sealing engagement between tongue 70 and peripheral lip 26. In addition guiding recess 80 is preferably positioned so that tongue 70 covers the entire chamber opening 28 when in a fully extended normally closed position. Finally, it should be noted that the housing and guiding recess 80 should be positioned so as not to substantially interfere with the direct manual operation of the primary closure mechanism cap 36.

As noted above, the secondary closure mechanism in this exemplary embodiment is a generally planar sliding tongue 70 having an external operating tab 74 in advance of a leading edge 72. Though the illustrated embodiment shows external operating tab 74 as vertically aligned in advance of leading edge 72 of tongue 70 and away from the horizontal chamber cover 24, it must be emphasized that alternative embodiments are contemplated by this invention. Any configuration allowing the manual and automatic lateral movement of the secondary closure tongue 70 is compatible. For example, operating tab 74 may project vertically downward or be slightly set back from leading edge 72 of tongue 70. As long as enough lateral movement of tongue 70 can be attained to expose opening 28 the configuration is within the scope of the present invention.

While laterally displaceable sliding tongue 70 is shown as being substantially planar, the portion of tongue 70 adjoining leading edge 72 may be tapered as illustrated at 82 to ensure an effective seal between vertically projecting peripheral lip 26 and tongue 70.

An exemplary biasing mechanism for secondary closure tongue 70 within housing recess 80 is illustrated in FIGS. 1, 3, 4, and 5. Tongue 70 is provided with an engagement tab 76 distally located with respect to leading edge 72 and positioned within housing recess 80. In the embodiment shown, tongue 70 rests on upper boss surface 56 with leading edge 72 and external operating tab 74 extending beyond the opening of housing recess 80. Engagement tab 76 is positioned to sit within elongated trough 46 running down the center of boss 40. A coil spring 84 is positioned within the recess formed by trough 46 and housing cover aperture 68 in compressive engagement with tab 76 to bias tongue 70 to a normally closed position extending out of guide recess 80 in sealing engagement with peripheral lip 26. While coil spring 84 is employed as the biasing mechanism in the illustrated embodiment, those skilled in the art will appreciate that a variety of other biasing mechanisms as known in the art may be used to practice the present invention. For example, torsion springs, hairpin springs or properly configured elastic materials and the like can be employed to bias tongue 70.

As shown in FIGS. 3 and 4, coil spring 84 is positioned in trough 46 contacting both engagement tab 76 and distal end wall 48 of boss 40. This simultaneous contact imparts a biasing force to tongue 70 through engaging tab 76, urging tongue 70 to assume an extended closed position. When the primary closure mechanism of cap 36 is removed this extended closed position effectively seals chamber opening 28 as illustrated in FIG. 3. Tongue 70 may be moved laterally within housing guide recess 80 by applying a force to external operating tab 74 sufficient to overcome the biasing force of spring 84. As shown in FIG. 4, the application of an external force represented by horizontal arrow 86 either manually or automatically by an automated dispensing system (not shown) to operating tab 74 laterally moves tongue 70 into housing guide recess 80 exposing chamber opening 28. FIG. 4 also shows the insertion of a transfer or dispensing apparatus such as aspirating tube 88 into chamber 22 through chamber opening 28 following this procedure. In the illustrated embodiment transfer mechanism 88 is positioned to come in proximity with fluid accumulation point 30.

While not illustrated, those skilled in the art will appreciate the general features of known automated dispensing systems used in concert with the present invention. Such systems may employ automatically controlled contact mechanisms to manipulate sample tubes, reagent containers or the like. These contact mechanisms typically consist of a dynamic cam, arm or the like controlled by the analyzer and powered by a solenoid or small motor. Upon receiving the appropriate signal from the controlling instrument or analyzer the contact mechanism may be moved by the solenoid or motor to apply a force to a properly positioned container.

The secondary closure mechanism of the present invention is specifically adapted to interact with such a contact mechanism. By providing external operating tab 74, laterally moveable tongue 70 may be manipulated depending on the immediate requirements of the clinical analyzer. More specifically the automatic contact mechanism of the dispensing apparatus (not shown) applies sufficient horizontal force 86 to operating tab 74 to overcome the bias of spring 84 and force laterally moveable tongue 70 to retract into housing guide recess 80. Reagent transfer mechanism 88 is then inserted by the automated dispenser or analyzer along the vertical axis of the container body through opening 28 into chamber 22. Following the transfer of the desired reagent and extraction of transfer mechanism 88, the contact mechanism is withdrawn to the point where it is no longer applying force to operating tab 74 on laterally moveable tongue 70. Upon withdrawal of the contact mechanism the bias of spring 84 returns tongue 70 to its normally closed position thereby engaging projecting peripheral lip 26 and sealing chamber opening 28. Those skilled in the art will appreciate that the secondary closure mechanism can be adapted to various configurations depending on the specific contact mechanism used in the automated dispensing system.

In FIGS. 3 and 4 engagement tab 76 is shown slightly angled with respect to the substantially horizontal plane defined by tongue 70. More specifically, engagement tab 76 is slightly angled toward leading edge 72 of the secondary closure mechanism. The force exerted by coil spring 84 simultaneously acting on distal end wall 48 of trough 46 and on engagement tab 76 urges the secondary closure mechanism into a fully extended position. Unless prevented by external force or a physical impediment such as the positioned primary closure mechanism of cap 36, tongue 70 will assume the normally closed extended position shown in FIG. 3.

When the secondary closure mechanism of exemplary tongue 70 is urged into the fully extended position as shown in FIG. 3, the force exerted by spring 84 pushes angled engagement tab 76 flush against substantially vertical proximate end wall 50 of trough 46. As the angled engagement tab 76 is pushed flush, the different angles of the engaging surfaces cause the laterally moveable tongue 70 to pivot. This pivot results in the leading edge 72 of tongue 70 arcing toward projecting peripheral lip 26 of chamber opening 28. Thus, the angled configuration of engagement tab 76 relative to substantially vertical end wall 50 translates the horizontal force of biasing spring 84 into a downward vertical force thereby improving the engagement tongue 70 with vertically projecting peripheral lip 26. Further, this is accomplished without substantially increasing the engagement friction between tongue 70 and projecting lip 26. The tapered portion 82 of tongue 70 assures that it will sit flush on projecting lip 26, effectively sealing chamber opening 28.

Similarly, the application of a horizontal external force as illustrated by arrow 86 in FIG. 4 on operating tab 74 causes laterally moveable tongue 70 to pivot about engagement tab 76 resting flush against proximate end wall 50. This pivoting action effectively lifts tongue 70 from projecting lip 26 clearing and exposing chamber opening 28 with little or no disengagement friction. As noted above, it should be emphasized that this horizontal force 86 may be applied manually or automatically through a controlled assembly guided by an instrument (not shown).

The secondary closure mechanism may also be employed to prevent the inadvertent loosening of cap 36. In FIG. 1 vertical friction ridges 38 on the exterior of cap 36 contact racheting pawl 78 provided on leading edge 72 of laterally moveable tongue 70. In the embodiment shown, racheting pawl 78 is positioned to the left of the center of leading edge 72 and primary closure mechanism cap 36 is tightened when rotated to the right or clockwise. As cap 36 is rotated clockwise pawl 78 is interposed between successive vertically disposed friction ridges 38 by the biasing force of spring 84 on engagement tab 76. Conversely, attempting to rotate cap 36 counterclockwise causes friction ridges 38 to catch on racheting pawl 78 and be retained. While not necessary to practice the present invention this racheting action prevents the inadvertent removal of primary closure mechanism cap 36 while pawl 78 is in contact with friction ridges 38. When the contact between pawl 78 and friction ridges 38 is disrupted manually, cap 36 may be removed easily by unscrewing. Those skilled in the art will appreciate that various embodiments of this mechanism may be employed to prevent the inadvertent loosening of cap 36.

Another advantage of the present invention is the ability to retain the primary closure mechanism in contact with container 10 when not in use. Though not essential for practicing the invention, this capacity reduces the chance of accidental reagent contamination. FIGS. 3 and 4 illustrate the placement of the removed internally threaded cap 36 on projecting cap retention lug 90 for cap storage purposes. In this position cap 36 also functions as a lifting handle to facilitate the removal of container 10 from an apparatus or dispenser. In the embodiment shown cap retention lug 90 is positioned on housing cover 62 and has substantially the same configuration as neck 32 with external threads 34. Alternative embodiments of the present invention may do without projecting lug 90 or may have a projection lug 90 suitable for holding the specific primary closure mechanism used to seal the container. Similarly, the placement of a cap retention mechanism is constrained only by potential interference with the operation of the present invention.

While the present invention has been depicted, described, and is defined by reference to a particular exemplary embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described embodiment of the invention is exemplary only, and is not exhaustive of the scope of the invention. Consequently, the invention is intended to be limited only by the spirit and scope of the appended claims, giving full cognizance to equivalents in all respects.

We claim:

1. A fluent material container for use in an automated dispensing system, said container comprising:

a sealingly covered chamber for containing a fluent material, said chamber provided with a generally horizontally disposed opening at its top, said opening being provided with an externally threaded neck defining a projecting peripheral lip;

a manually operable internally threaded screw cap disposed upon said neck for releasably sealing said opening;

manually operable secondary closing means for releasably sealing said opening subsequent to the removal of said screw cap and adapted to mechanically interface with said automated dispensing system; and means for biasing said secondary closing means to a normally closed position covering said opening and sealingly engaging said projecting peripheral lip.

2. The fluent material container of claim 1 further comprising an externally threaded lug projecting from said fluent material container and adapted to receive said internally threaded screw cap subsequent to the removal of said screw cap from said externally threaded neck.

3. A fluent material container for use in an automated dispensing system, said container comprising:

a sealingly covered chamber for containing a fluent material, said chamber provided with a generally horizontally disposed opening at its top, said opening having a vertically projecting peripheral lip;

manually operable, removable primary closing means for releasably sealing said opening;

manually operable secondary closing means, including a laterally displaceable, generally planar sliding tongue disposed within a generally horizontal guiding recess provided on the top of said sealingly covered chamber adjacent to said opening, said tongue adapted to sealingly engage said projecting peripheral lip when extended from said guiding recess, for releasably sealing said opening subsequent to the removal of said primary closing means and adapted to mechanically interface with said automated dispensing system; and means for biasing said secondary closing means to a normally closed position covering said opening and sealingly engaging said projecting peripheral lip.

4. The fluent material container of claim 3 wherein said means for biasing said secondary closing means is a spring disposed within said horizontal guiding recess in compressive engagement with said sliding tongue.

5. The fluent material container of claim 3 wherein said vertically projecting peripheral lip defines a generally circular opening edge.

6. The fluent material container of claim 5 wherein said tongue is provided with a tapered leading edge and is angled to slidingly engage said opening edge.

7. The fluent material container of claim 6 wherein said primary closing mechanism is an internally threaded screw cap provided with a plurality of generally vertically disposed external friction ridges and said tapered leading edge of said sliding tongue is provided with a racheting pawl adapted to engage said plurality of generally vertically disposed friction ridges.

8. The fluent material container of claim 6 wherein said sliding tongue is provided with an operating tab adapted to mechanically interface with an automated dispensing system.

9. A liquid reagent container for use in an automated dispensing system, said container comprising:

a sealingly covered substantially wedge shaped chamber for containing a liquid reagent, said chamber provided with an externally threaded neck defining a generally circular horizontally disposed opening having a projecting peripheral lip;

a manually operable internally threaded removable screw cap threaded onto said neck for releasably sealing said opening and having a plurality of vertically disposed friction ridges;

a manually operable, laterally displaceable, substantially planar sliding tongue disposed within a generally horizontal guiding recess provided on top of said chamber for releasably sealing said opening subsequent to the removal of said screw cap and adapted to mechanically interface with an automated dispensing system; and a biasing spring disposed within said horizontal guiding recess in compressive engagement with said sliding tongue and biasing said tongue to a normally closed position covering said opening and sealingly engaging said projecting peripheral lip.

10. The liquid reagent container of claim 9 wherein said sliding tongue is provided with a tapered leading edge and is angled downwardly toward said projecting peripheral lip.

11. A fluent reagent container for use in an automated dispensing system, said container comprising:

a sealingly covered chamber for containing a fluent reagent, said chamber provided with an externally threaded neck defining a generally horizontally disposed opening having a projecting peripheral lip;

a manually operable, removable internally threaded screw cap on said neck for releasably sealing said opening, said cap having a plurality of generally vertically disposed friction ridges on its exterior surface;

a manually operable secondary closure for releasably sealing said opening subsequent to the removal of said screw cap and adapted to mechanically interface with an automated dispensing system, said secondary closure disposed within a generally horizontal guiding recess provided on the top of said container; and a biasing spring disposed within said horizontal guiding recess in compressive engagement with said secondary closing means and biasing said secondary closing means to a normally closed position covering said opening and sealingly engaging said projecting peripheral lip subsequent to the removal of said screw cap from said neck.

12. The fluent reagent container of claim 11 wherein said secondary closure is a laterally displaceable, generally planar sliding tongue, said tongue adapted to sealingly engage said projecting peripheral lip when extended from said guiding recess.

13. The fluent reagent container of claim 12 wherein said sliding tongue is provided with a tapered leading edge and is angled downwardly toward said projecting peripheral lip.

14. The fluent reagent container of claim 11 wherein said sealingly covered chamber is wedge shaped.

15. The fluent reagent container of claim 13 wherein said tapered leading edge of said sliding tongue is provided with a rachet pawl adapted to engage said plurality of friction ridges on said screw cap.

16. The fluent reagent container of claim 13 wherein said sliding tongue is provided with an operating tab affixed to said leading edge and adapted to mechanically interface with an automated dispensing system.

17. The fluent reagent container of claim 11 wherein said externally threaded neck defines a generally circular opening.

18. The fluent reagent container of claim 11 further comprising an externally threaded lug projecting from said liquid reagent container and adapted to receive said internally threaded screw cap subsequent to the removal of said screw cap from said externally threaded neck.

* * * * *